United States Patent [19]

Garner

[11] Patent Number: 4,991,958
[45] Date of Patent: Feb. 12, 1991

[54] MICROPIPETTE ADAPTOR FOR SPECTROPHOTOMETERS

[75] Inventor: Harold R. Garner, Encinitas, Calif.
[73] Assignee: General Atomics, San Diego, Calif.
[21] Appl. No.: 377,476
[22] Filed: Jul. 10, 1989
[51] Int. Cl.[5] .............................................. G01N 21/01
[52] U.S. Cl. ..................................... 356/244; 356/434
[58] Field of Search ......................... 356/244, 246, 434
[56] References Cited

U.S. PATENT DOCUMENTS 4,006,990 2/1977 Munk .............................. 356/434 X Primary Examiner—Davis L. Willis
Assistant Examiner—Matthew W. Koren
Attorney, Agent, or Firm—Nydegger & Associates

[57] ABSTRACT

An adaptor for holding a micropipette in a spectrophotometer includes a base member for holding the micropipette and an optical system for linearly focusing visible or ultraviolet light onto the micropipette. Specifically, the optical system includes a cylindrical lens which focuses collimated light from a light source into a line along the axis of the micropipette. The optical system also includes a cylindrical quartz lens which recollimates the light that has passed through the micropipette sample holder. A detector is provided to receive the recollimated light for measuring the absorptivity of the sample material held in the micropipette.

19 Claims, 1 Drawing Sheet

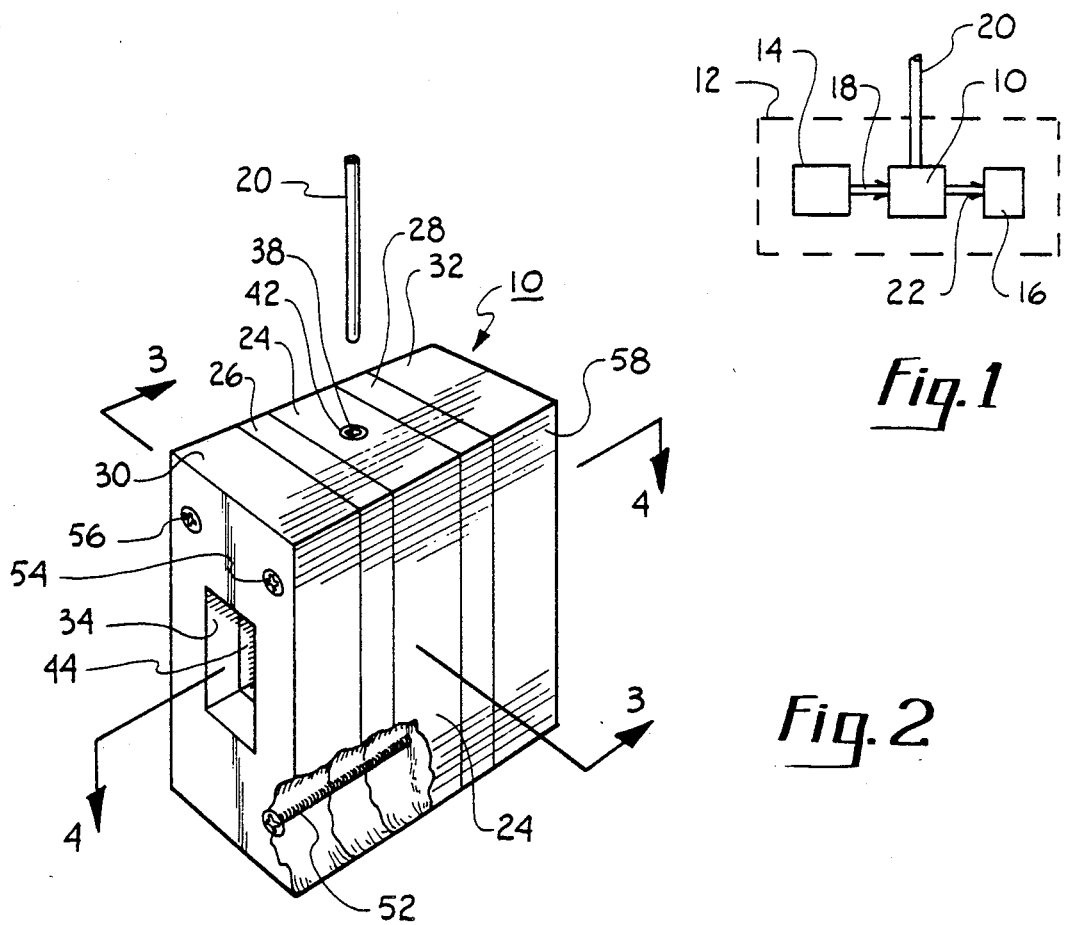
Fig. 1
Fig. 2
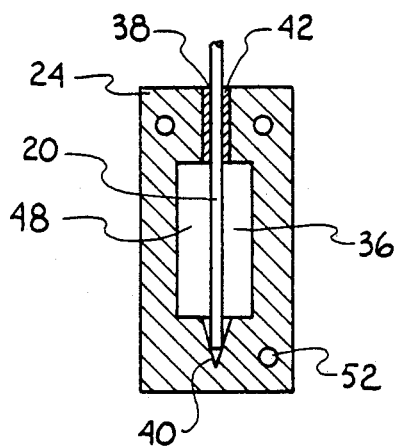
Fig. 3
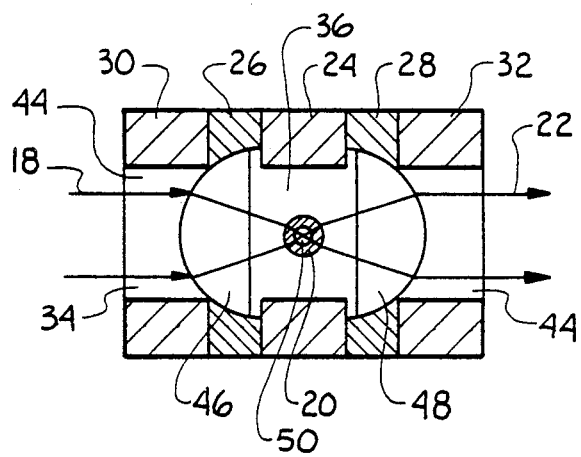
Fig. 4

MICROPIPETTE ADAPTOR FOR SPECTROPHOTOMETERS

FIELD OF THE INVENTION

The present invention pertains to devices which hold sample materials while the composition of the material is being measured and analyzed. Specifically, the present invention pertains to sample holders which may be used with spectrophotometers and colorimeters. The present invention is particularly, but not exclusively, useful for obtaining spectroscopic measurements of very small samples of material.

BACKGROUND OF THE INVENTION

The use of spectrophotometers to measure the light absorption characteristics of sample materials is well known. Indeed, the basic principles involved are relatively simple. A beam of light, whose characteristics are known, is directed through the sample material and the light that emerges is analyzed to determine which wavelengths of the original beam were absorbed, or otherwise affected, by the sample material. Based on differences between the incident light and the transmitted light, certain characteristics of the sample material can be determined. Many variables are involved, however, that can make a spectrophotometric measurement quite complex. In sum, these complexities arise from the fact that the sensitivity and accuracy of a measurement rely on the ability of the spectrophotometer to measure the light which is absorbed by the samples.

Analytically, a spectrophotometric analysis relies on a known relationship of the variables involved. Specifically, in a standard spectrophotometric measurement, the amount of light transmitted through a test cuvette is measured and the percent of transmitted light is related to the material in the cuvette by the following relationship:

$$I_t(\lambda) = I(\lambda) 10^{-OD}$$

where $I(\lambda)$ and $I_t(\lambda)$ are respectively the input and transmitted intensities, and the optical density, OD, is given by:

$$OD = \alpha(\lambda) L C$$

where $\alpha(\lambda)$ is the absorptivity of the material as a function of $\lambda$, L is the optical path length, and C is the concentration. From the above, it will be easily appreciated that the output intensity $I_t(\lambda)$ is directly proportional to the input intensity $I_o(\lambda)$. Therefore, it is clearly necessary to have an input intensity that is sufficient to give an output intensity which can be effectively used for analysis and measurement of the sample material. Further, the efficacy of the measurement will also be enhanced if the concentration of the sample material is increased. Thus, for spectrophotometric analysis it is desirable to have a light input of high intensity, and have a highly concentrated sample in solution. There is a problem, however, when low concentration solutions of sample material are available in only very small quantities (e.g. 0.5 to 50 micrograms/microliter).

To be effective for spectroscopic measurements, test cuvettes for holding the sample material must be completely filled. This typically requires a substantial amount of sample material. Consequently, when only a small amount of the sample material is effectively available for testing, presently available test cuvettes (e.g. 12.5 mm × 12.5 mm cuvette) are inadequate because of their relatively large size. Merely reducing the size of the cuvette is not the answer. This is so because, with a size reduction of the cuvette there is also a reduction in the amount of sample material through which light can pass. Consequently, the intensity of the light passing through the sample material is reduced and the sensitivity and accuracy of the measurement is compromised.

The present invention recognizes that it is possible to take spectrophotometric measurements of very small quantities of a sample material, even where there is a relatively low concentration of the material in solution. The present invention recognizes that this can be done by properly focusing collimated light onto the sample material to obtain sufficiently high input light intensities for the desired measurements. Further, the present invention recognizes that this focusing can be accomplished by a device which is engageable, and operatively compatible, with presently available spectrophometers such as a UVIKON Model 820 spectrophotometer by Kontron.

In light of the above, it is an object of the present invention to provide a micropipette adaptor for spectrophotometers which allows for spectrophotometric measurements of very small quantities of sample material in solution. Another object of the present invention is to provide a micropipette adaptor for spectrophotometers which permits recovery of the sample material after spectrophotometric measurements have been made. Yet another object of the present invention is to provide a micropipette adaptor for spectrophotometers which allows spectroscopic measurements of samples to be made while the sample is in the process of being transferred in a micropipette. Still another object of the present invention is to provide a micropipette adaptor for spectrophotometers which provides for a high light collection efficiency to increase the sensitivity of the measurements which are made. Another object of the present invention is to provide a micropipette adaptor for spectrophotometers which allows a micropipette or other capillary sample holder to be easily installed and removed from the adaptor. Yet another object of the present invention is to provide a micropipette adaptor for spectrophotometers which provides approximately the same intensity light path length product for small samples as is provided for larger samples. Another object of the present invention is to provide a micropipette adaptor for spectrophotometers which is relatively easy to manufacture and comparatively cost-effective to operate.

SUMMARY OF THE INVENTION

The micropipette adaptor for spectrophotometers according to the present invention comprises a base member which is adapted to hold a capillary tube, such as a micropipette, which is filled with a solution of the sample material to be analyzed More specifically, the base member is formed with an opening, and is formed with a hole which is distanced across the opening from a conical well. As formed on the base member, both the hole and the conical well are aligned with each other to respectively receive a portion of the micropipette and hold it on the base member. When so held, the micropipette extends across the opening of the base member to permit light to pass through the micropipette.

An optical system is provided for the adaptor and is attached to the base member to both focus a beam of collimated light onto the micropipette, and to recollimate the light that has passed through the micropipette.

For focusing the beam of collimated light, a cylindrical quartz lens (i.e. a directing lens) is positioned between the base member and the source of collimated visual or ultraviolet light. Specifically, this directing lens is used to focus collimated light from the light source into a line. In accordance with the present invention, this linearly focused light is aligned along the longitudinal axis of the micropipette to provide a very high intensity light input for the sample material which fills the lumen of the micropipette. Another cylindrical quartz lens (i.e. a receiving lens) is positioned behind the base member to receive the light which has passed through the sample material in the pipette and to recollimate it for analysis and measurement by a detector As contemplated by the present invention, both the directing lens and the receiving lens are respectively held by holders which are positioned on opposite sides of the base member. Importantly, each of these holders is independently adjustable in its position relative to the base member. Thus, the directing lens may be independently moved relative to the micropipette to achieve alignment of its linearly focused light with the axis of the micropipette. Similarly, the receiving lens may be moved relative to the micropipette to achieve effective recollimation of the light that has passed through the micropipette. This recollimated light is then received by a detector in the spectrophotometer for further spectroanalysis. It will be appreciated by the skilled artisan that, depending on the wavelength of the light, the receiving lens and the directing lens may be made of quartz, glass, sapphire, fused silicon or any other appropriate light transmitting material.

As contemplated by the present invention, the adaptor is intended for use with very small micropipettes. For example, it is within the contemplation of the present invention that a micropipette having a capillary tube with a lumen which is approximately half a millimeter (0.5 mm) in diameter can be effectively used with the adaptor disclosed herein. Even so, it will be appreciated by the skilled artisan that pipettes of various sizes may be used. Furthermore, it is to be appreciated that the light wavelengths which are useful with the adaptor of the present invention need not necessarily be limited to the visual and ultraviolet ranges.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a schematic diagram showing the micropipette adaptor in its operative relationship with elements of a spectrophotometer;

FIG. 2 is a perspective view of the micropipette adaptor with selected elements shown in phantom and portions broken away for clarity;

FIG. 3 is a cross-sectional view of the micropipette adaptor as seen along the line 3—3 in FIG. 2; and FIG. 4 is a cross-sectional view of the micropipette adaptor as seen along the line 4—4 in FIG. 2.

DESCRIPTION OF THE PREFERRED EMBODIMENT

Referring initially to FIG. 1, the micropipette adaptor for spectrophotometers in accordance with the present invention is schematically shown in its operative environment and is designated 10. As shown, adaptor 10 is positioned for operative engagement with a spectrophotometer 12 and, specifically, is positioned between a light source 14 and a detector 16. As so positioned, an input beam of collimated light 18, having an intensity $I_o(\lambda)$, is directed from the light source 14 toward the adaptor 10. In a manner to be subsequently disclosed, adaptor 10 focuses the beam 18 of collimated light onto a micropipette 20 which is held by the adaptor 10. Adaptor 10 then recollimates this light into an output light beam 22 which has an intensity of $I_f(\lambda)$. As will be appreciated by the skilled artisan, the difference between $I_o(\lambda)$ and $I_f(\lambda)$ is indicative of the light absorption characteristics of the sample material held in micropipette 22 and, hence, is an indication of the composition of the sample material.

The construction of adaptor 10 will, perhaps, be best seen by reference to FIG. 2 wherein it is shown that adaptor 10 comprises a base member 24 which is sandwiched between a resilient member 26 and a resilient member 28. Respectively positioned against resilient members 26 and 28 and opposite base member 24 are holders 30 and 32. Preferably, base member 24 and the holders 30 and 32 are made of a rigid material, such as black delrin plastic, while the resilient members 26 and 28 are made of an elastomeric material such as rubber or foam plastic. For purposes of the present invention, holder 30 is formed with an opening 34 as shown in FIG. 2, and base member 24, resilient members 26, 28 and holder 32 are each formed with openings (not shown in FIG. 2) which are aligned with opening 34 to establish a pathway 44 which allows light to pass through adaptor 10.

Referring now to FIG. 3, it will be seen that base member 24 is formed with an opening 36 which, as indicated above, is positioned in alignment with opening 34 of holder 30. Further, base member 24 is shown formed with a hole 38 and a conical-shaped well 40 which are positioned across the opening 36 from each other. Specifically, hole 38 and conical well 40 respectively receive portion of micropipette 20 to hold the micropipette 20 in place within and across the opening 36. A bushing 42, which is appropriately sized to receive micropipette 20, may be positioned in hole 38 to securely hold the micropipette on adaptor 10.

As best seen in FIG. 4, the base member 24, together with its adjacent resilient members 26, 28 and the holders 30, 32 are all positioned with their respective openings aligned to create a pathway 44 through adaptor 10 along which light can shine. FIG. 4 also shows that a lens 46 is positioned in pathway 44. Specifically, lens 46 is attached or mounted on holder 30 by any means well known in the pertinent art, such as by gluing or solvent bonding. Further, lens 46 may be mounted on holder 30 by a frictional snap-in configuration or held thereon by set screws (not shown). Similarly, a lens 48 is attached or mounted on holder 32 and is positioned in the pathway 44 substantially as shown. For purposes of the present invention, it is preferable that the lenses 46, 48 be cylindrical. This is so in order for the lens 46 (the directing lens) to linearly focus input light beam 18 onto a line which can be positioned along the longitudinal axis of micropipette 20. Further, a cylindrical shape for lens 48 (the receiving lens) is also preferable in order for the linearly focused input light beam 18 to be recollimated as output light beam 22. Preferably, both cylindrical lens 46 and cylindrical lens 48 are made of a quartz material which permits use of either visible or ultraviolet light.

As will be appreciated by the skilled artisan, input light beam 18 can be precisely focused along the longitudinal axis of micropipette 20 by appropriately moving lens 46 in a direction along the pathway 44. In order to linearly focus input light beam 18 and obtain the highest intensity $I_0(\lambda)$ for the light which is incident on the sample material being held in micropipette 20, the holder 30 on which lens 46 is mounted, can be moved relative to the base member 24 on which micropipette 20 is mounted. As seen in FIG. 4, when lens 46 is properly positioned, input beam 18 will be focused into a line which is coincident with the center of lumen 50 of micropipette 20. Following well known optical principles, light will emerge from micropipette 20 in a predictable fashion. Consequently, cylindrical lens 48 (the receiving lens) can receive this emerging light and recollimate the light into the output light beam 22. To accomplish this, lens 48 is mounted on holder 32 and is movable therewith relative to base member 24. As will be readily appreciated, the resilient members 26, 28 permit selective relative movement between base member 24 and the respective holders 30, 32. At the same time, resilient members 26, 28 provide a support for maintaining the relative positions of these components when they are not being moved. It is possible, however, to completely eliminate the resilient members 26, 28. Manufacturing tolerances may suffice to properly position lens 46 on holder 30 without any further adjustment necessary to predictably focus light from the lens 46 along the interior lumen of micropipette 20. Similarly, lens 48 may be mounted on holder 32 and positioned relative to base member 24 without the need for subsequent adjustments.

The mechanism for moving holders 30, 32 relative to base member 24 will be best seen by referring to FIG. 2 wherein a screw 52 is shown extending through holder 30 and resilient member 26 for threadable connection with base member 24. The screws 54 and 56 likewise connect holder 30 with base member 24. Similarly, screws (of which the screw 58 shown in phantom is exemplary) connect holder 32 with base member 24. In each case, the screws 52, 54, 56, 58 (and others not shown) can be individually rotated to independently move the holders 30, 32 relative to the base member 24. Consequently, this moves lenses 46, 48 relative to micropipette 20.

As intended for the present invention, movement of cylindrical lens 46 relative to micropipette 20 is accomplished to linearly focus input light beam 18 along the axis of micropipette 20. This increases the intensity $I_0(\lambda)$ of the light which is incident on the sample material held in solution in lumen 50 of micropipette 20. Similarly, movement of the cylindrical lens 48 relative to micropipette 20 is accomplished in order to recollimate the light which emerges from micropipette 20 for easier analysis of its intensity $I_f(\lambda)$ by the detector 16.

While the particular micropipette adaptor for spectrophotometers as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An adaptor for holding a micropipette in a spectrophotometer having a source of collimated light and a detector which comprises:
    a base member formed with a first hole and a conical well distanced from said first hole, said conical well being aligned with said first hole and cooperating therewith to hold said micropipette;
    a directing lens for linearly focusing the collimated light from said light source along the axis of said micropipette; and
    a receiving lens to recollimate the light passed through said micropipette for measurement by said detector.

2. An adaptor for holding a micropipette in a spectrophotometer having a source of collimated light and a detector as recited in claim 1 wherein said directing lens is a cylindrical quartz lens.

3. An adaptor for holding a micropipette in a spectrophotometer having a source of collimated light and a detector as recited in claim 2 wherein said receiving lens is a clyindrical quartz lens.

4. An adaptor for holding a micropipette in a spectrophotometer having a source of collimated light and a detector as recited in claim 1 further comprising a bushing positioned in said first hole for securely holding said micropipette on said base member.

5. An adaptor for holding a micropipette in a spectrophotometer having a source of collimated light and a detector as recited in claim 1 further comprising a holder for holding said directing lens and a holder for holding said receiving lens.

6. An adaptor for holding a micropipette in a spectrophotometer having a source of collimated light and a detector as recited in claim 5 further comprising means for moving said directing lens holder relative to said base member to linearly focus said collimated light from said light source in axial alignment onto said micropipette.

7. An adaptor for holding a micropipette in a spectrophotometer having a source of collimated light and a detector as recited in claim 6 further comprising means for moving said receiving lens holder relative to said base member to recollimate the light which has passed through said micropipette.

8. An adaptor for holding a micropipette in a spectrophotometer having a source of collimated light and a detector as recited in claim 7 further comprising a resilient member disposed on one side of said base member between said base member and said directing lens holder and another resilient member disposed on another side of said base member between said base member and said receiving lens holder to stabilize said holders relative to said base member.

9. An adaptor for holding a micropipette in a spectrophotometer having a source of collimated light and a detector as recited in claim 1 wherein said light is visible light.

10. An adaptor for holding a micropipette in a spectrophotometer having a source of collimated light and a detector as recited in claim 1 wherein said light is ultraviolet light.

11. An apparatus for analyzing a sample solution held in a micropipette which comprises:
    a source of collimated light;
    a directing lens to linearly focus collimated light from said light source;
    a base for holding said micropipette in axial alignment with the linearly focused light, said base having a first hole and a conical well, said conical well being distanced from said first hole and aligned with said first hole and cooperating therewith to hold said micropipette, said base further comprising a bushing positioned in said first hole for securely holding said micropipette on said base;

a receiving lens for recollimating light which has passed through said micropipette; and a detector for measuring said recollimated light to determine the light absorption characteristics of said sample.

12. An apparatus for analyzing a sample solution held in a micropipette as recited in claim 11 wherein said directing lens and said receiving lens are clyindrical quartz lenses.

13. An apparatus for analyzing a sample solution held in, a micropipette as recited in claim 11 further comprising:

a holder for holding said directing lens and a holder for holding said receiving lens;

means for moving said directing lens holder relative to said base member to linearly focus said collimated light from said light source in axial alignment onto said micropipette; and means for moving said receiving lens holder relative to said base member to recollimate the light which has passed through said micropipette.

14. An apparatus for analyzing a sample solution held in a micropipette as recited in claim 13 wherein said moving means are screws for respectively movably connecting said receiving lens holder with said base member and movably connecting said directing lens holder with said base member.

15. An apparatus for analyzing a sample solution held in a micropipette as recited in claim 13 wherein said base member, said directing lens holder and said receiving lens holder are made of plastic.

16. An apparatus for analyzing a sample solution held in a micropipette as recited in claim 13 further comprising a resilient member disposed on one side of said base member between said base member and said directing lens holder and another resilient member disposed on another side of said base member between said base member and said receiving lens holder to stabilize said holders relative to said base member.

17. An apparatus for analyzing a sample solution held in a micropipette as recited in claim 16 wherein said resilient members are made of rubber.

18. A method for determining the light absorptivity of a minute sample solution held in an elongated hollow cylindrical micropipette which comprises the steps of:

producing a beam of collimated light;

holding said micropipette on a base member;

positioning said micropipette in the path of said beam of collimated light;

juxtaposing a directing cylindrical quartz lens with said base member to linearly focus said beam into axial alignment with said micropipette;

moving a receiving cylindrical quartz lens relative to said base member to recollimate the light which has passed through said micropippette; and measuring the recollimated light to determine the absorption characteristics of said sample.

19. A method for determining the light absorptivity of a minute sample solution held in an elongated hollow cylindrical micropipette as recited in claim 18 wherein said producing step is accomplished by producing a beam of either visible or ultraviolet light.

* * * * *